(12) United States Patent
Lee et al.

(10) Patent No.: US 8,282,552 B2
(45) Date of Patent: Oct. 9, 2012

(54) ADAPTIVE IMAGE FILTERING IN AN ULTRASOUND IMAGING DEVICE

(75) Inventors: Jae Keun Lee, Seoul (KR); Suk Jin Lee, Seoul (KR)

(73) Assignee: Medison Co., Ltd., Kangwon-do (KR)

( * ) Notice: Subject to any disclaimer, the term of this patent is extended or adjusted under 35 U.S.C. 154(b) by 903 days.

(21) Appl. No.: 12/274,269

(22) Filed: Nov. 19, 2008

(65) Prior Publication Data

US 2009/0131787 A1 May 21, 2009

(30) Foreign Application Priority Data

Nov. 20, 2007 (KR) .................. 10-2007-0118600

(51) Int. Cl.
*A61B 8/00* (2006.01)
(52) U.S. Cl. ............ 600/437; 73/628; 73/631; 382/132
(58) Field of Classification Search .......... 600/437–463; 382/128–132; 73/603–628
See application file for complete search history.

(56) References Cited

U.S. PATENT DOCUMENTS

| | | | |
|---|---|---|---|
| 5,050,226 A | | 9/1991 | Collet-Billon |
| 5,999,639 A | * | 12/1999 | Rogers et al. .................. 382/132 |
| 6,091,841 A | * | 7/2000 | Rogers et al. .................. 382/132 |
| 6,115,488 A | * | 9/2000 | Rogers et al. .................. 382/132 |
| 6,137,898 A | * | 10/2000 | Broussard et al. ............ 382/132 |
| 6,167,146 A | * | 12/2000 | Rogers et al. .................. 382/132 |
| 6,205,236 B1 | * | 3/2001 | Rogers et al. .................. 382/132 |
| 6,389,157 B2 | * | 5/2002 | Rogers et al. .................. 382/132 |
| 6,468,218 B1 | | 10/2002 | Chen et al. |
| 6,556,699 B2 | * | 4/2003 | Rogers et al. .................. 382/132 |
| 6,650,766 B1 | * | 11/2003 | Rogers et al. .................. 382/132 |
| 6,804,381 B2 | * | 10/2004 | Pang et al. ..................... 382/111 |
| 6,910,380 B2 | * | 6/2005 | Ogawa ............................ 73/628 |
| 6,970,587 B1 | * | 11/2005 | Rogers ........................... 382/132 |
| 7,308,126 B2 | * | 12/2007 | Rogers et al. .................. 382/132 |
| 7,556,602 B2 | * | 7/2009 | Wang et al. ..................... 600/437 |

(Continued)

FOREIGN PATENT DOCUMENTS

EP 0 543 386 A2 5/1993
KR 10-2005-0097298 A 10/2005

OTHER PUBLICATIONS

Korean Notice of Allowance issued in Korean Patent Application No. 10-2007-011860, dated May 31, 2011.

(Continued)

*Primary Examiner* — Sanjay Cattungal
(74) *Attorney, Agent, or Firm* — McDermott Will & Emery LLP

(57) ABSTRACT

The present invention relates to an ultrasound imaging device. The ultrasound imaging device includes: a data acquiring unit for acquiring 3-dimensional ultrasound image data based on receive signals formed based on ultrasound echoes reflected from a target object; a filtering unit for determining a size of a filtering mask of a filter, said size being adaptively determined according to an amount of the 3-dimensional ultrasound image data in data acquisition directions, the filtering unit being further configured to filter the 3-dimensional ultrasound image data by using the filtering mask; a scan converting unit for scan-converting the filtered 3-dimensional ultrasound image data; and a 3-dimensional rendering unit for performing 3-dimensional rendering upon the scan-converted 3-dimensional ultrasound image data to form a 3-dimensional ultrasound image.

8 Claims, 4 Drawing Sheets

U.S. PATENT DOCUMENTS

| | | | |
|---|---|---|---|
| 2001/0008562 A1* | 7/2001 | Rogers et al. | 382/132 |
| 2002/0054293 A1* | 5/2002 | Pang et al. | 356/430 |
| 2002/0081006 A1* | 6/2002 | Rogers et al. | 382/128 |
| 2003/0097068 A1 | 5/2003 | Hossack et al. | |
| 2004/0187583 A1* | 9/2004 | Ogawa | 73/628 |
| 2005/0123181 A1* | 6/2005 | Freund et al. | 382/128 |
| 2005/0240104 A1 | 10/2005 | Shim et al. | |
| 2005/0259854 A1* | 11/2005 | Arimura et al. | 382/130 |
| 2006/0171573 A1* | 8/2006 | Rogers | 382/128 |
| 2007/0083114 A1* | 4/2007 | Yang et al. | 600/437 |

OTHER PUBLICATIONS

European Search Report issued in Application No. 08020149.4 issued on Apr. 27, 2012.

* cited by examiner

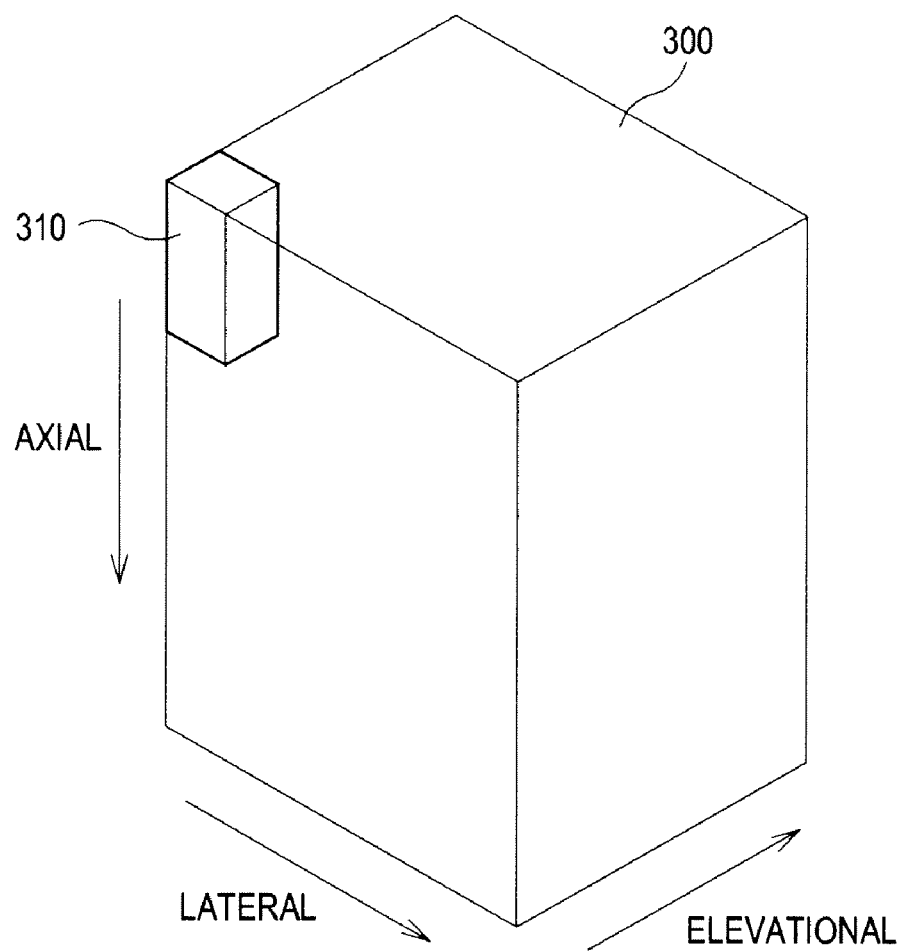

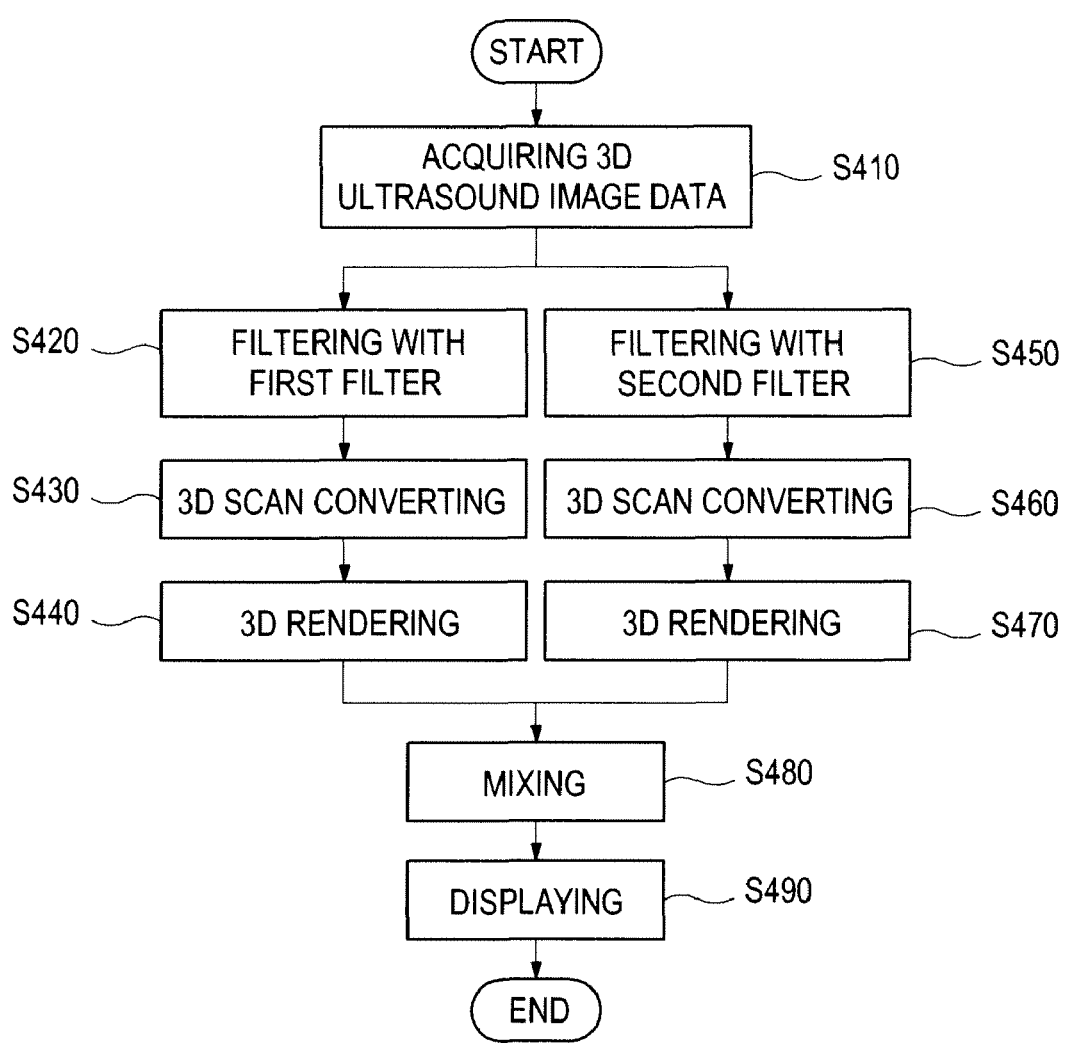

ADAPTIVE IMAGE FILTERING IN AN ULTRASOUND IMAGING DEVICE

The present application claims priority from Korean Patent Application No. 10-2007-0118600 filed on Nov. 20, 2007, the entire subject matter of which is incorporated herein by reference.

BACKGROUND OF THE INVENTION

1. Technical Field

The present invention generally relates to an ultrasound imaging device, and more particularly to an ultrasound imaging device and a method of forming a 3-dimensional ultrasound image using an adaptive filter.

2. Background Art

An ultrasound imaging device has become an important and popular diagnostic tool due to its non-invasive and non-destructive nature. The ultrasound imaging device may form an ultrasound image by using ultrasound characteristics such as reflection, scattering and absorption when the ultrasound signals are propagated into tissues of a human body. Since the reflection and scattering of the ultrasound signals simultaneously occur in the target object, speckle noises may be included in forming ultrasound image data. The speckle noises may degrade a 3-dimensional ultrasound image. Also, boundaries between the organs and a background, which are important portions for diagnosis, may not be correctly displayed due to the speckle noises. Thus, the speckle noises may be burdensome in analyzing the 3-dimensional ultrasound image and examining the organs in the 3-dimensional ultrasound image.

Recently, various types of filters have been introduced to reduce the speckle noises in the 3-dimensional ultrasound image. However, the conventional filters may filter the 3-dimensional ultrasound data without considering an amount of data in data acquisition directions (i.e., axial, lateral and elevation directions) to reduce the speckle noises. As such, a loss of the ultrasound image data may occur during the filtering. Thus, the 3-dimensional ultrasound image may be distorted due to the data loss.

BRIEF DESCRIPTION OF THE DRAWINGS

FIG. 3 is a schematic diagram showing an example of a filtering mask set in 3-dimensional ultrasound image data.

FIG. 4 is a flowchart showing an example of mixing ultrasound images filtered by filters with different filtering masks.

DETAILED DESCRIPTION OF THE INVENTION

Figure 1:
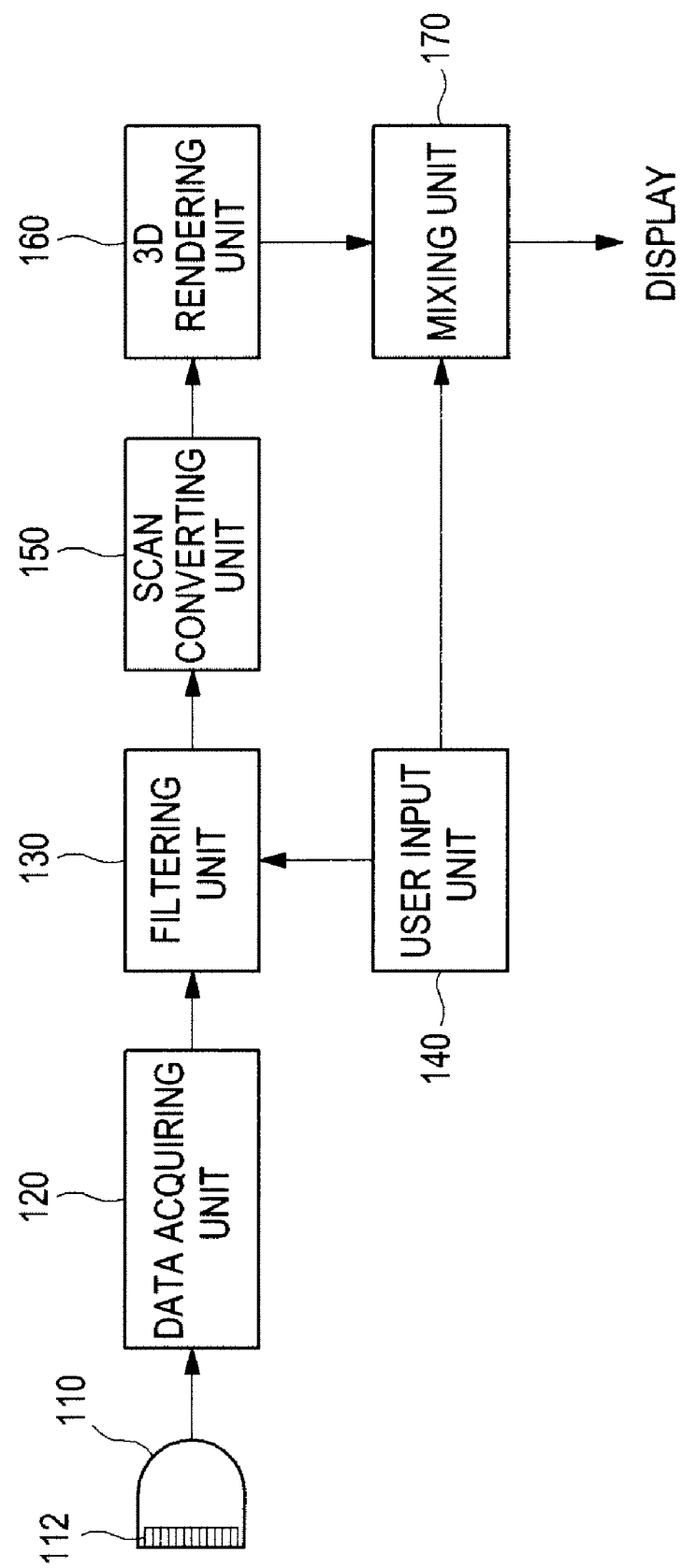
FIG. 1 is a block diagram showing one embodiment of the ultrasound imaging device.

FIG. 1 is a block diagram of an illustrative embodiment of an ultrasound imaging device. Referring to FIG. 1, a probe 100 may include a plurality of elements 112. The elements 112 may transmit ultrasound signals along scan lines set in a target object in response to transmit pulse signals applied thereto. The elements 112 may then output electrical receive signals based on ultrasound echoes reflected from the target object.

Figure 2:
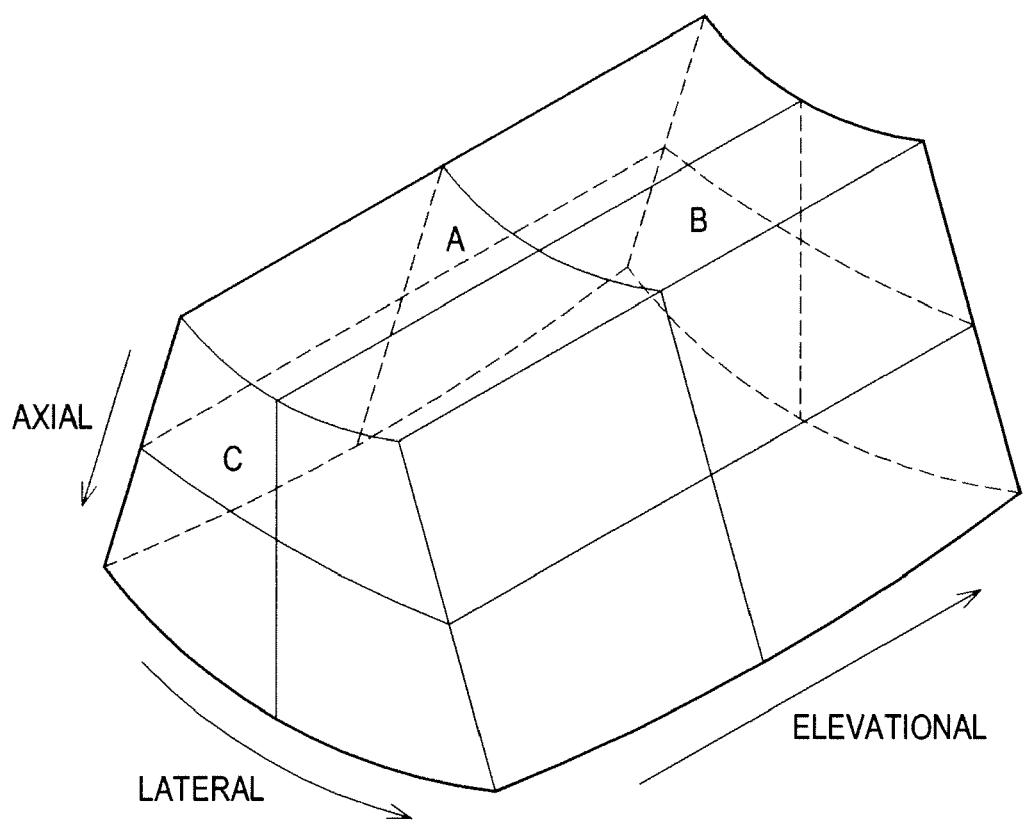
FIG. 2 is a schematic diagram showing an example of 3-dimensional ultrasound image data acquired in axial, lateral and elevation directions.

A data acquiring unit 120 may perform signal processing upon the receive signals to thereby form ultrasound image data. The ultrasound image data may include a 3-dimensional ultrasound image data such as volume data, as illustrated in FIG. 2. Reference planes A, B and C may be set in the volume data. The reference planes A, B and C may be determined based on a scanning direction. A resolution of reference plane images may depend on the amount of ultrasound image data, which are acquired during the scanning. Generally, a larger amount of ultrasound image data may be acquired in the order of an axial direction, a lateral direction and an elevation direction.

A filtering unit 130 may filter the ultrasound image data to reduce speckle noises in the ultrasound image data. In one embodiment, the filtering unit 130 may adopt an adaptive 3-dimensional filter. The adaptive 3-dimensional filter may use a filtering mask, the size of which is determined according to a data acquisition ratio of the ultrasound image data in data acquisition directions. The filter unit 130 may calculate a data acquisition ratio of amounts of the ultrasound image data in axial, lateral and elevation directions. The filtering unit 130 may determine a size of the filtering mask of the adaptive 3-dimensional filter in the axial, lateral and elevation directions to obtain the same ratio as the data acquisition ratio. For example, assuming that the data acquisition ratio is 7:5:3 in the axial, lateral and elevation directions, the filtering unit 130 may determine the filtering mask having a size of 7×5×3.

FIG. 3 is a schematic diagram showing an example of a filtering mask set on the 3-dimensional ultrasound image data 300. As shown in FIG. 3, a length of the filtering mask 310 in an axial direction, for which a relatively more amount of ultrasound image data may be obtained, may be set to be relatively long. Also, a length of the filtering mask 310 in an elevation direction, for which a relatively less amount of ultrasound image data may be obtained, may be set to be relatively short. Thus, data loss may be reduced during the filtering. In one embodiment, the filter may be an average filter or a Gaussian filter. That is, the filtering unit 130 may be configured to smooth the ultrasound image through the filtering to thereby reduce the speckle noises.

A user input unit 140 may receive an instruction from a user. The user input unit 140 may be an input device such as a keyboard, a mouse, a track ball and the like. As mentioned above, the size of the filtering mask may be determined according to the amount of the ultrasound data for the respective data acquisition directions in accordance with one embodiment. Also, in another embodiment, the size of the filtering mask may be determined by the instruction inputted through the user input unit 140. That is, the user may adjust the size of the filtering mask so that a desirable ultrasound image may be obtained.

The scan converting unit 150 may scan-convert the filtered ultrasound image data into a data format suitable for display. The scan converting unit 150 may perform 3-dimensional scan conversion. A 3-dimensional rendering unit 160 may perform volume rendering upon the scan-converted ultrasound image data to thereby form a 3-dimensional ultrasound image. The volume rendering may be carried out with a ray casting method. The 3-dimensional ultrasound image data obtained through the volume rendering may be interpolated to form a 3-dimensional ultrasound image. The 3-dimensional ultrasound image may be displayed on a display unit (not shown).

In another embodiment, the 3-dimensional ultrasound image data may be filtered at least twice with the filtering masks having different sizes. The filtered 3-dimensional ultrasound image data may be scan-converted and rendered. This is so that a plurality of 3-dimensional ultrasound images obtained by using different filtering masks may be obtained.

The plurality of 3-dimensional ultrasound images may be mixed to obtain a desirably smoothened 3-dimensional ultrasound image. To this end, the ultrasound imaging device 100 may further comprise a mixing unit 170 for mixing the 3-dimensional ultrasound images produced by the 3-dimensional rendering unit 160.

FIG. 4 is a flowchart showing a procedure of forming an ultrasound image by mixing ultrasound images filtered with different sizes of the filtering masks. Referring to FIG. 4, the data acquiring unit 120 may acquire the ultrasound image data based on the receive signals outputted from the probe 110. The filtering unit 130 may filter the ultrasound image data with a first filtering mask to thereby output a first filtered ultrasound image data at step S420. In such a case, the size of the first filtering mask may be determined according to a ratio of amounts of the ultrasound image data in the axial, lateral and elevation directions. That is, the size of the first filtering mask may be determined to have the same ratio as the data acquisition ratio in the axial, lateral and elevation directions. Also, in another embodiment, the size of the filtering mask may be determined by the user instruction inputted through the user input unit 140.

The scan converting unit 150 may scan-convert the first filtered ultrasound image data to output a first scan-converted ultrasound image data at step S430. The 3-dimensional rendering unit 160 may perform the volume rendering upon the first scan-converted ultrasound image data to thereby form a first ultrasound image data at step S440.

Subsequently, the filtering unit 130 may filter the ultrasound image data with a second filtering mask to thereby output a second filtered ultrasound image data at step S450. In such a case, the size of the filtering mask may be determined to have a larger size than the first filtering mask. The size of the second mark filter may also be determined to have the same ratio as the data acquisition ratio in the axial, lateral and elevation directions. Moreover, the size of the second filtering mask may be determined by the user instruction inputted through the user input unit 140.

The scan converting unit 150 may scan-convert the second filtered ultrasound image data to output a second scan-converted ultrasound image data at step S460. The 3-dimensional rendering unit 160 may perform the volume rendering upon the second scan-converted ultrasound image data to thereby form a second ultrasound image at step S470.

The mixing unit 170 may mix the first and second ultrasound images to thereby form a final 3-dimensional ultrasound image at step S480. A mixing ratio of the first and second ultrasound images may be determined by a user instruction inputted through the user input unit 140. For example, if the mixing ratio of the first ultrasound image is higher, then a relatively sharper ultrasound image may be obtained. Also, if the mixing ratio of the second ultrasound image is higher, then a relatively more smoothened ultrasound image may be obtained. The mixed 3-dimensional ultrasound image may be displayed through the display unit at step S490. According to another embodiment, the more smoothened 3-dimensional ultrasound image may be obtained.

As mentioned above, since the size of the filtering mask is adaptively adjusted according to the data acquisition ratio in the axial, lateral and elevation directions, the data loss may be reduced with a reduction of the speckle noise. Thus, an enhanced 3-dimensional ultrasound image may be obtained. Further, as the adaptive filtering mask is adopted, filtering calculation may be reduced.

In accordance with one embodiment of the present invention, there is provided an ultrasound imaging device, comprising: a data acquiring unit for acquiring 3-dimensional ultrasound image data based on receive signals formed based on ultrasound echoes reflected from a target object; a filtering unit for determining a size of a filtering mask of a filter, said size being adaptively determined according to an amount of the 3-dimensional ultrasound image data in data acquisition directions, the filtering unit being further configured to filter the 3-dimensional ultrasound image data by using the filtering mask; a scan converting unit for scan-converting the filtered 3-dimensional ultrasound image data; and a 3-dimensional rendering unit for performing 3-dimensional rendering upon the scan-converted 3-dimensional ultrasound image data to form a 3-dimensional ultrasound image.

In accordance with another embodiment of the present invention, there is provided a method of forming an ultrasound image, comprising: a) acquiring 3-dimensional ultrasound image data based on ultrasound echoes reflected from a target object; b) adaptively determining a size of a filtering mask of a filter according to an amount of the 3-dimensional ultrasound image data in data acquisition directions and filtering the 3-dimensional ultrasound image data by using the filtering mask; c) scan-converting the filtered 3-dimensional ultrasound image data; and d) performing 3-dimensional rendering upon the scan-converted 3-dimensional ultrasound image data to form a 3-dimensional ultrasound image.

Any reference in this specification to "one embodiment," "an embodiment," "example embodiment," etc. means that a particular feature, structure or characteristic described in connection with the embodiment is included in at least one embodiment of the present invention. The appearances of such phrases in various places in the specification are not necessarily all referring to the same embodiment. Further, when a particular feature, structure or characteristic is described in connection with any embodiment, it is submitted that it is within the purview of one skilled in the art to effect such feature, structure or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound imaging device, comprising:
   a data acquiring unit configured to acquire 3-dimensional ultrasound image data based on receive signals formed based on ultrasound echoes reflected from a target object;
   a filtering unit configured to determine a size of a filtering mask of a filter, said size being adaptively determined according to an amount of the 3-dimensional ultrasound image data in data acquisition directions, the filtering unit being further configured to filter the 3-dimensional ultrasound image data by using the filtering mask having the determined size to reduce speckle noise;
   a scan converting unit configured to scan-convert the filtered 3-dimensional ultrasound image data; and a 3-dimensional rendering unit configured to perform 3-dimensional rendering upon the scan-converted 3-dimensional ultrasound image data to form a 3-dimensional ultrasound image, wherein the filtering unit is configured to determine the size of the filtering mask according to a data acquisition ratio of an amount of the 3-dimensional data in data acquisition directions, and wherein the size of the filtering mask is determined to have different lengths in at least two acquisition directions.

2. The ultrasound imaging device of claim 1, further comprising a user input unit operable to an instruction for setting the size of the filtering mask.

3. The ultrasound imaging device of claim 1, further comprising a mixing unit configured to mix a plurality of ultrasound images.

4. The ultrasound imaging device of claim 3, wherein the filtering unit is configured to filter the 3-dimensional ultrasound image data with a first filtering mask to thereby output a first filtered ultrasound image data and a second filtering mask having a different size from the first filtering mask to thereby output a second filtered ultrasound image data, the scan converting unit is configured to scan-convert the first and second filtered ultrasound image data to output first and second scan-converted ultrasound image data, the 3-dimensional rendering unit is configured to perform rendering upon the first and second scan-converted ultrasound image data to thereby form first and second 3-dimensional ultrasound images, and the mixing unit is configured to mix the first and second 3-dimensional ultrasound images to form a single 3-dimensional ultrasound image.

5. The ultrasound imaging device of claim 4, wherein the second filtering mask is larger than the first filtering mask.

6. A method of forming an ultrasound image, comprising:
a) acquiring 3-dimensional ultrasound image data based on ultrasound echoes reflected from a target object;
b) adaptively determining a size of a filtering mask of a filter according to an amount of the 3-dimensional ultrasound image data in data acquisition directions and filtering the 3-dimensional ultrasound image data by using the filtering mask having the determined size to reduce speckle noise;
c) scan-converting the filtered 3-dimensional ultrasound image data; and
d) performing 3-dimensional rendering upon the scan-converted 3-dimensional ultrasound image data to form a 3-dimensional ultrasound image, wherein the size of the filtering mask is determined according to a ratio of amount of the 3-dimensional data in data acquisition directions, and wherein the size of the filtering mask is determined to have a different length in at least two acquisition directions.

7. The method of claim 6, wherein the step b) includes filtering the 3-dimensional ultrasound image data with a first filtering mask to thereby output a first filtered ultrasound image data and a second filtering mask having a different size from the first filtering mask to thereby output a second filtered ultrasound image data, the step c) includes scan-converting the first and second filtered ultrasound image data to output first and second scan-converted ultrasound image data, and the step d) includes performing rendering upon the first and second scan-converted ultrasound image data to thereby form first and second 3-dimensional ultrasound images, the method further comprising mixing the first and second 3-dimensional ultrasound images to form a single 3-dimensional ultrasound image.

8. The method of claim 7, wherein the second filtering mask is larger than the first filtering mask.

* * * * *